United States Patent [19]

Bartels

[11] Patent Number: 5,152,898

[45] Date of Patent: * Oct. 6, 1992

[54] SEPARATION OF ORGANIC OXYGENATES

[75] Inventor: Craig R. Bartels, Wappingers Falls, N.Y.

[73] Assignee: Texaco Inc., White Plains, N.Y.

[*] Notice: The portion of the term of this patent subsequent to Feb. 12, 2008 has been disclaimed.

[21] Appl. No.: 437,430

[22] Filed: Nov. 16, 1989

Related U.S. Application Data

[63] Continuation-in-part of Ser. No. 425,156, Oct. 23, 1989, Pat. No. 4,992,176.

[51] Int. Cl.$^5$ .............................................. B01D 61/36
[52] U.S. Cl. ............................ 210/640; 159/DIG. 27; 159/49; 203/89; 210/500.27; 210/500.37; 210/654
[58] Field of Search ..................... 203/89, 86; 159/DIG. 27, DIG. 28, 49; 210/640, 654, 500.37, 500.27, 644, 649; 568/913

[56] References Cited

U.S. PATENT DOCUMENTS

| | | | |
|---|---|---|---|
| 4,036,808 | 7/1977 | Rembaum et al. | 210/735 |
| 4,102,827 | 7/1978 | Rembaum et al. | 210/736 |
| 4,154,909 | 5/1979 | Seita et al. | 521/32 |
| 4,410,638 | 10/1983 | Bachot et al. | 521/27 |
| 4,444,571 | 4/1984 | Matson | 55/49 |
| 4,664,681 | 5/1987 | Anazawa et al. | 55/16 |
| 4,666,991 | 5/1987 | Matsui et al. | 525/276 |
| 4,758,342 | 7/1988 | Heckmann et al. | 210/500.21 |
| 4,798,674 | 1/1989 | Pastanak et al. | 568/913 |
| 4,876,403 | 10/1989 | Cohen et al. | 568/913 |
| 4,877,528 | 10/1989 | Friesen et al. | 55/16 |
| 4,877,529 | 10/1989 | Pasternak et al. | 210/500.37 |
| 4,992,176 | 2/1991 | Bartels | 210/654 |

FOREIGN PATENT DOCUMENTS 0096339 12/1983 European Pat. Off.
0161109 7/1986 Japan.

OTHER PUBLICATIONS

"Effect of Quarternization on the Pervaporation Rate of Water Through Poly(4-Vinylpyridine) Membrane", Hamaya and Yamada, in Kobinishi Ronbushu, 34 (7), 545–547, 1977.

"Complex Formation of Crosslinked Poly (4-Vinylpyridine) Resins with Copper (II)" Nishide, Deguchi and Tsuchida Bulletin of the Chem. Lab Society of Japan, vol. 9 (12) 3498–3501 (1976).

"Mobility of Spin Probes in Quarternized Poly (4-Vinylidinine) Membranes" Makino, Hamada, and Lijima in Polyn. J. (Tokyo), 19(6), 737–745, 1987.

"Separation of Some Aqueous Amine Solutions by Pervaporation Through Poly (4-Vinylpyridine) Membrane" Yamada and Hamaya Kobunshi Ronbunshu, 39(6), 407–414, 1982.

Primary Examiner—Virginia Manoharan
Attorney, Agent, or Firm—Robert A. Kulason; James J. O'Loughlin; Carl G. Seutter

[57] ABSTRACT

Concentration of solutions containing methanol and either dimethyl carbonate or methyl t-butyl ether may be effected by a composite membrane including a dibromobutane cross-linked poly(4-vinyl pyridine) bonded to a porous layer of polyacrylonitrile on a polyester backing.

16 Claims, No Drawings

SEPARATION OF ORGANIC OXYGENATES

This application is a continuation-in-part of application Ser. No. 07/425,156 filed Oct. 23, 1989 by Texaco Inc as assignee of Craig R. Bartels, now U.S. Pat. No. 4,992,176 issued Feb. 12, 1991.

FIELD OF THE INVENTION

This invention relates to the separation of organic oxygenates such as methyl alcohol. More particularly it relates to a membrane technique for effecting separation of methanol from reaction mixtures containing methanol together with products such as methyl t-butyl ether or dimethyl carbonate.

BACKGROUND OF THE INVENTION

As well known to those skilled in the art, it is possible to separate mixtures of liquids by various techniques including adsorption or distillation. These conventional processes, particularly distillation, are however, characterized by high capital cost. In the case of distillation for example the process requires expensive distillation towers, heaters, heat exchangers (reboilers, condensers, etc.), together with a substantial amount of auxiliary equipment typified by pumps, collection vessels, vacuum generating equipment, etc.

Such operations are characterized by high operating costs principally costs of heating and cooling—plus pumping, etc.

Furthermore the properties of the materials being separated, as is evidenced by the distillation curves, may be such that a large number of plates may be required, etc. When the material forms an azeotrope with water, additional problems may be present which for example, would require that separation be effected in a series of steps (e.g. as in two towers) or by addition of extraneous materials to the system.

There are also comparable problems which are unique to adsorption systems.

It has been found to be possible to utilize membrane systems to separate mixtures of miscible liquids by pervaporation. In this process, the charge liquid is brought into contact with a membrane film; and one component of the charge liquid preferentially permeates the membrane The permeate is then removed as a vapor from the downstream side of the film—typically by sweeping with a carrier gas or by reducing the pressure below the saturated vapor pressure of the permeating species.

Illustrative membranes which have been employed in prior art techniques include those set forth in the following table:

TABLE

| Separating Layer | References |
|---|---|
| Nafion brand of perfluorosulfonic acid | Cabasso and Liu J. Memb. Sci. 24, 101 (1985) |
| Sulfonated polyethylene | Cabasso, Korngold & Liu J. Pol. Sc: Letters, 23, 57 (1985) |
| Fluorinated polyether or Carboxylic Acid fluorides | USP 4,526,948 to Dupont as assignee of Resnickto |
| Selemion AMV brand of Asahi Glass cross-linked styrene butadiene (with quaternary ammonium residues on a polyvinyl chloride backing) | Wentzlaff Boddeker & Hattanbach J. Memb. Sci. 22,333 (1985) |
| Cellulose triacetate | Wentzlaff, Boddeker & Hattanback, J. Memb. Sci. 22, 333 (1985) |
| Polyacrylonitrile | Neel, Aptel & Clement Desalination 53, 297 (1985) |
| Crosslinked Polyvinyl Alcohol | Eur. Patent 0 096 339 to GFT as assignee of Bruschke |
| Poly(maleimide-acrylonitrile) | Yoshikawa et al J. Pol. Sci. 22, 2159 (1984) |
| Dextrine - isophorone diisocyanate | Chem. Econ. Eng. Rev., 17, 34 (1985) |

The cost effectiveness of a membrane is determined by the selectively and productivity. Of the membranes commercially available, an illustrative polyvinyl alcohol membrane of high performance is that disclosed in European patent 0 096 339 A2 of GFT as assignee of Bruschke—published Dec. 21, 1983.

European Patent 0 096 339 A2 to GFT as assignee of Bruschke discloses, as cross-linking agents, diacids (typified by maleic acid or fumaric acid); dihalogen compounds (typified by dichloroacetone or 1,3-dichloroisopropanol); aldehydes, including dialdehydes, typified by formaldehyde. These membranes are said to be particularly effective for dehydration of aqueous solutions of ethanol or isopropanol.

This reference discloses separation of water from alcohols, ethers, ketones, aldehydes, or acids by use of composite membranes. Specifically the composite includes (i) a backing typically about 120 microns in thickness, on which is positioned (ii) a microporous support layer of a polysulfone or a polyacrylonitrile of about 50 microns thickness, on which is positioned (iii) a separating layer of cross-linked polyvinyl alcohol about 2 microns in thickness.

Polyvinyl alcohol may be cross-linked by use of difunctional agents which react with the hydroxyl group of the polyvinyl alcohol. Typical cross-linking agent may include dialdehydes (which yield acetal linkages), diacids or diacid halides (which yield ester linkages), dihalogen compounds or epichlorhydrin (which yield ether linkages) olefinic aldehydes (which yield ether/acetal linkages), boric acid (which yields boric ester linkages), sulfonamidoaldehydes, etc.

See also J. G. Prichard, *Polyvinyl Alcohol, Basic Properties and Uses*, Gordon and Breach Science Publishers, New York (1970) or C. A. Finch, *Polyvinyl Alcohol, Properties and applications*, John Wiley and Sons, New York (1973) or U.S. Pat. No. 4,798,674 to Pasternak, Bartels, and Reale.

U.S. Pat. No. 4,728,429 to Cabasso et al, U.S. Pat. No. 4,067,805 to Chiang et al, U.S. Pat. No. 4,690,766 to Linder et al provide additional background.

Additional prior art which may be of interest includes:

*Mobility of Spin Probes in Quaternized Poly(4-Vinylpyridine) Membranes*, Makino, Hamada, and Iijima, in Polym. J. (Toyko), 19(6), 737–45, 1987.

*Effect of Quaternization on the Pervaporation Rate of Water Through Poly(4-Vinylpyridine) Membrane*, Hamaya, and Yamada, in Kobunshi Ronbunshu, 34(7), 545–7, 1977.

*Preparation of Separation Membranes*, Yamamoto, Toi, and Mishima, patent #JP 61/161109 A2, Jul 21 1986. (Japanese).

*Separation of Some Aqueous Amine Solutions by Pervaporation through Poly(4-Vinylpyridine) Membrane* Yamada and Hamaya, in Kobunshi Ronbunshu, 39(6), 407-14, 1982.

*Complex Formation of Crosslinked Poly(4-Vinylpyridine) Resins with Copper (II)*, by Nishide, Deguchi, and Tsuchida, in Bulletin of the Chemical Society of Japan, Vol. 49 (12), 3498-3501 (1976).

It is an object of this invention to provide a novel separation process. Other objects will be apparent to those skilled in the art.

STATEMENT OF THE INVENTION

In accordance with certain of its aspects, this invention is directed to a method of concentrating a charge solution containing (i) an alcohol having less than three carbon atoms and (ii) an organic oxygenate selected from the group consisting of organic ethers, aldehydes, ketones, and esters which comprises maintaining a non-porous separating layer of poly(vinyl pyridine) which has been cross-linked with an aliphatic polyhalide;

maintaining a pressure drop across said non-porous separating layer of poly(vinyl pyridine);

passing a charge solution containing (i) an alcohol having less than three carbon atoms and (ii) an organic oxygenate selected from the group consisting of organic ethers, aldehydes, ketones, and esters into contact with the high pressure side of said non-porous separating layer whereby at least a portion of said alcohol in said charge solution and a lesser portion of organic oxygenate in said charge solution pass by pervaporation through said non-porous separating layer as a lean mixture containing more alcohol and less organic oxygenate than are present in said charge solution and said charge solution is converted to a rich liquid containing less alcohol and more organic oxygenate than are present in said charge solution;

recovering as permeate from the low pressure side of said non-porous separating layer said lean mixture containing more alcohol and less organic oxygenate than are present in said charge solution, said lean mixture being recovered in vapor phase at a pressure below the vapor pressure thereof; and recovering as retentate from the high pressure side of said non-porous separating layer said rich liquid containing a lower alcohol content and a higher organic oxygenate content than are present in said charge solution.

DESCRIPTION OF THE INVENTION

The composite structure of this invention includes a multi-layer assembly which in the preferred embodiment preferably includes a porous carrier layer which provides mechanical strength and support to the assembly.

THE CARRIER LAYER

This carrier layer, when used, is characterized by its high degree of porosity and mechanical strength. It may be fibrous or non-fibrous, woven or non-woven. In the preferred embodiment, the carrier layer may be a porous, flexible, non-woven or woven fibrous polyester.

One typical non-woven polyester carrier layer may be formulated of non-woven, thermally-bonded strands and characterized by a fabric weight of 80±8 grams per square yard, a thickness of 4.2±0.5 mils, a tensile strength (in the machine direction) of 31 psi and (in cross direction) of 10 psi, and a Frazier air permeability of 6 cuft/min/sq. ft. @0.5 inches of water.

THE POROUS SUPPORT LAYER

The porous support layer of this invention is preferably formed of a sheet or membrane of polysulfone polymer, polyvinylidene fluoride, a teflon polyfluoroethylene polymer, or more preferably of polyacrylonitrile. Typically the support layer may be of thickness of 40-80 microns, say 50 microns and of molecular weight $\overline{M}_n$ of 5 000-100,000, preferably 20,000-60,000 say 40,000. The polyacrylonitrile is preferably characterized by a pore size of less than about 500A and typically about 200A. This corresponds to a molecular weight cut-off of less than about 100,000, typically about 20,000.

THE SEPARATING LAYER

The separating layer which permits attainment of the separation in accordance with this invention may include a non-porous film of cross-linked poly(vinyl pyridine) of thickness of about 1-10 microns, preferably 1-5 microns, say 3 microns. The layer is formed preferably by casting from a poly(4-vinyl pyridine)—typically the Reilline 4200 brand (of Reilly Tar and Chemical Co) of poly-4-vinyl pyridine) in a 10 w% solution in a suitable solvent such as an alcohol, typical methanol.

The membrane may be formed by mixing 0.5-2 parts, say 1 part of the 10%-30%, say 20 w% solution of poly(4-vinyl pyridine) in methanol with 1 part methanol, and 0.1-0.8 parts, say 0.52 parts, parts of aliphatic polyhalide cross-linking agent.

It is a feature of this invention that the separating layer may be a homopolymer or a copolymer of 2-vinyl pyridine or 4-vinyl pyridine. When copolymers are employed, the co-monomer may be an ethlenically unsaturated monomer, typically vinyl chloride, ethylene, vinyl acetate, styrene, vinyl acetate, vinyl alcohol, acrylonitrile or ethylene oxide, etc. In the preferred embodiment, the separating layer is a homopolymer of 4-vinyl pyridine of molecular weight $\overline{M}_v$ of 10,000-500,000, preferably 100,000-300,000, say about 200,000.

The polymer may be cross-linked with a cross-linking agent to form the membranes useful in practice of this invention.

Typically the cross-linking agents may contain an aliphatic moiety, preferably containing 2-12 carbon atoms, typically 3-6 carbon atoms, say 4 carbon atoms. Although the cross-linking agent may be a polyhalide, it typically contains 2-5 halogen atoms, most preferably 2. The halogen is preferably bromine or less preferably chlorine or iodine. The halides may preferably be alpha, omega dihalides of linear straight chain aliphatic hydrocarbon. Typical cross-linking agents may be as tabulated infra, the first listed being preferred:

TABLE 1,4-dibromo-n-butane
1,5-dibromo-n-pentane
1,10-dibromo-decane
1,4-dichloro-n-butane
1,3-dibromo-n-pentane
1,6-dibromo-n-hexane
1,8-dibromo-octane In situ cross-linking may be carried out by casting onto the preferred polyacrylonitrile support the poly(4-vinyl pyridine) typically in the 10 w % solution in methanol to which is added the cross-linking agent (typically 1,4-dibromobutane) in mole ratio of cross-linking agent to polymer repeat unit of 0.2–2, say about 1.13.

It may be possible in one embodiment to cross-link the poly(4-vinyl pyridine) separating layer in one step by adding to the solution of poly(4-vinyl pyridine) and polyhalide, followed by heat curing.

In another embodiment, it may be possible to apply to the porous support layer, a solution of poly(4-vinyl pyridine) in an alcohol solvent. This may be dried at 40° C. –80° C., say 50° C. for 2–10 minutes, say 4 minutes to form a film. The polyvinyl pyridine may then be cross-linked by soaking the film in an alcohol solution containing 1–50%, say 10% of a polyhalide cross-linking agent.

The composite membrane, whether prepared by the one-step or the two-step process may then be cured in an oven at 100° C.–200° C., say 125° C. for 1–30 minutes, say 2 minutes to yield a polyvinyl alcohol film having a thickness of 1–10 microns, say 4 microns.

THE COMPOSITE MEMBRANE

It is a feature of this invention that the composite membrane of this invention may comprise (i) an optional carrier layer, characterized by porosity and mechanical strength, for supporting a porous support layer and a separating layer, (ii) a porous support layer of preferably polyacrylonitrile of molecular weight of 5,000–100,000, of thickness of 10–80 microns, and of molecular weight $\overline{M}_n$ cut off of 20,000–200,000 and (iii) as a non-porous separating layer poly(vinyl pyridine) of molecular weight of 20,000–400,000 which has been cross-linked with an aliphatic polyhalide.

The composite membranes of this invention may be utilized in various configurations. It is, for example, possible to utilize the composite in a plate-and-frame configuration in which separating layers may be mounted on the porous support layer with the carrier layer.

It is possible to utilize a spiral mound module which includes a non-porous separating layer membrane mounted on a porous support layer and a carrier layer, the assembly being typically folded and bonded or sealed along all the edges but an open edge—to form a bag-like unit which preferably has the separating layer on the outside. A cloth spacer, serving as the permeate or discharge channel is placed within the bag-like unit. The discharge channel projects from the open end of the unit.

There is then placed on one face of the bag-like unit, adjacent to the separating layer, and coterminous therewith, a feed channel sheet—typically formed of a plastic net.

The so-formed assembly is wrapped around a preferably cylindrical conduit which bears a plurality of perforations in the wall—preferably in a linear array which is as long as the width of the bag-like unit. The projecting portion of the discharge channel of the bag-like unit is placed over the performations of the conduit; and the bag-like unit is wrapped around the conduit to form a spiral wound configuration.

It will be apparent that, although only one feed channel is present, the single feed channel in the wound assembly will be adjacent to two faces of the membrane layer. The spiral wound configuration may be formed by wrapping the assembly around the conduit a plurality of times to form a readily handleable unit. The unit is fitted within a shell(in manner comparable to a shell-and-tube heat exchanger) provided with an inlet at one end and an outlet at the other. A baffle-like seal between the inner surface of the shell and the outer surface of the spiral-wound input prevents fluid from bypassing the operative membrane system and insures that fluid enters the system principally at one end. The permeate passes from the feed channel, into contact with the separating layer and thence therethrough, into the permeate channel and thence therealong to and through the perforations in the conduit through which it is withdrawn as net permeate.

In use of the spiral wound membrane, charge liquid is permitted to pass through the plastic net which serves as a feed channel and thence into contact with the non-porous separating membranes. The liquid which does not pass through the membranes is withdrawn as retentate. The liquid or vapor which permeates the membrane passes into the volume occupied by the permeate spacer and through this permeate channel to the perforations in the cylindrical conduit through which it is withdrawn from the system. In this embodiment, it will be apparent that the system may not include a carrier layer.

In another embodiment, it is possible to utilize the system of this invention as a tubular or hollow fiber. In this embodiment, the porous support layer of e.g. polyacrylonitrile may be extruded as a fine tube with a wall thickness of typically 0.001–0.1 mm. The extruded tubes are passed through a bath of poly(vinyl pyridine) which is cross-linked and cured in situ. A bundle of these tubes is secured (with an epoxy adhesive) at each end in a header; and the fibers are cut so that they are flush with the ends of the header. This tube bundle is mounted within a shell in a typical shell-and-tube assembly.

In operation, the charge liquid is admitted to the tube side and passes through the inside of the tubes and exits as retentate. During passage through the tubes, permeate passes through the non-porous separating layer and permeate is collected in the shell side.

In this embodiment, it will be apparent that the system may not normally include a carrier layer. In still another embodiment, the porous support layer may be omitted; and the separating layer is extruded and thereafter cross-linked and cured in situ prior to mounting in the headers.

PERVAPORATION

It is a feature of the non-porous separating layer that it is found to be particularly effective when used in a pervaporation process. In pervaporation, a charge liquid containing a more permeable and a less permeable component is maintained in contact with a non-porous separating layer; and a pressure drop is maintained across that layer. The charge liquid dissolves into the membrane and diffuses therethrough. The permeate which passes through the membrane and exits as a vapor may be recovered by condensing at low temperature or alternatively may be swept away by use of a moving stream of gas. Preferably, the permeate side of the membrane is maintained at a low pressure, typically 5 mm. Hg.

For general background on pervaporation, note U.S. Pat. Nos. 4,277,344; 4,039,440; 3,926,798; 3,950,247; 4,035,291; etc.

It is a feature of this invention that the novel membrane may be particularly useful in pervaporation processes for concentrating a charge solution containing (i) an alcohol and (ii) oxygenate selected from the group consisting of organic ethers, aldehydes, ketones, and esters.

The oxygenate may be (i) an organic ether such as dimethyl ether, diethyl ether, di-n-propyl ether, di-n-butyl ether, methyl t-butyl ether, ethyl t-butyl ether, methyl t-amyl ether, ethyl t-amyl ether, etc.;

(ii) an aldehyde such as acetaldehyde, propionaldehyde, butyraldehyde, benzaldehyde, etc.;

(iii) a ketone such as acetone, methyl ethyl ketone, diethyl ketone, etc.; or (iv) an ester such as methyl acetate, methyl propionate, methyl butyrate, methyl benzoate, dimethyl carbonate, diethyl carbonate, etc.

The alcohol may typically be methanol, ethanol, n-propanol, i-propanol, butanols, pentanols, hexanols, etc.

Most favorable results may be obtained with the water-soluble lower alkanols, most preferably methanol.

It will be obvious to those skilled in the art that the process of this invention may find particular use when the charge mixture to be treated is a reaction product wherein one of the components to be separated is unreacted charge component. A typical such charge mixture is that attained from the reaction of methanol and carbon monoxide wherein the mixture may contain unreacted methanol and product dimethyl carbonate (DMC). Another illustrative charge mixture is that attained from the reaction of methanol and isobutene wherein the reaction mixture may contain methanol and methyl t-butyl ether (MTBE).

These charge solutions may have been subjected to preliminary separation, e.g. distillation, to yield, for example, an azeotrope of methanol and dimethyl carbonate.

Other charge solutions may include (i) methyl acetate-methanol, (ii) ethyl acetate-ethanol, etc.

In practice of the pervaporation process of this invention, the charge solution typically at 40° C.-120° C., say 70° C. may be passed into contact with the non-porous separating layer of the membrane of this invention. A pressure drop of about one atmosphere is commonly maintained across the membrane. Typically, the feed or charge side of the membrane is at about atmospheric pressure and the permeate or discharge side of the membrane is at a pressure of about 0.5-50 preferably 5-20, say 1.5 mm.Hg, or lower.

The permeate which passes through the membrane typically includes e.g. methanol and a small proportion of the oxygenate from the charge liquid. Typically, the permeate contains 90-99 w %, say up to 99 w % methanol. Permeate is recovered in vapor phase.

Pervaporation may typically be carried out at a flux of 0.1-5, say about 3 kilograms per square meter per hour (kmh). Typically, the units may have a selectivity (measured in terms of w % of e.g. methanol in the permeate during pervaporation at 70° C. of a ca 30 w % solution of oxygenate through a standard polyvinyl pyridine separating layer of 3 microns thickness) of 90-99.9 w % methanol. It will vary depending on the oxygenate.

Practice of the process of this invention will be apparent to those skilled in the art from inspection of the following examples wherein, as elsewhere in this specification, all parts are parts by weight unless otherwise stated. An asterisk indicates a control example.

DESCRIPTION OF SPECIFIC EMBODIMENTS

Example I

In this example, which represents the best mode presently known of carrying out the process of this invention, the selective separating layer is mounted on the porous support layer of a commercially available (under the trademark DUY-L, from Daicel Corp) composite containing a woven polyester backing as carrier layer, bearing as porous support layer, a microporous polyacrylonitrile layer of molecular weight cut-off of 40,000.

The separating layer is formed by applying to the porous support layer, a 10 w % solution in methanol of the Reilline 4200 brand (available from Reilly Company) of poly(4-vinyl pyridine) containing 20 w % of 1,4-dibromobutane. Mole ratio of cross-linking agent to polymer is 1.13. The coated support is placed in an oven at 125° C. for 2 minutes to dry and cure the film.

The membrane made by this method is evaluated in a pervaporation cell to which the charge is admitted at 60° C. Permeate pressure is 8 torr at liquid nitrogen temperature.

In this preferred embodiment, the charge solution is a solution containing 31.7 w % dimethyl carbonate (DMC) and 68.3 w % methanol. The permeate flux is 3.82 kmh and contained 4.7 w % DMC which represents a Separation Factor of 10. This flux is over three times greater than the best flux obtained in U.S. Pat. No. 4,798,674 and the Separation Factor is higher.

EXAMPLES II-VIII

In this series of Examples, the procedure of Example I is followed except:

(i) In Examples II and VI, the mole ratio MR is 0.86;

(ii) In Examples IV and VII, the mole ratio MR is 1.39;

(iii) In Examples V and VIII, the cross-linking agent is 1,5-dibromopentane and the mole ratio MR of cross-linking agent to polymer is 0.81;

(iv) In Examples II-V, the charge contain 29.7 w % of DMC and 70.3 w % of methanol;

(v) In Examples II-V, the feed temperature is 50° C.

The following Table sets forth the mole ratio (MR) of cross-linking agent to polymer; the temperature ° C. and time (minutes) of curing; the feed concentration w % DMC; the permeate concentration w % DMC; the Flux in kilograms per square meter per hour (kmh); and the Separation Factor Sep.

TABLE

Support: Daicel DUY-L polyacrylonitrile
Reilline 4200, ca 20 w % poly(4-vinyl pyridine) solids in MeOH
Coating: 3 mil

| Example | MR | FD CNC % | PM CNC % | FLUX | SEP |
|---|---|---|---|---|---|
| I | 1.13 | 31.7 | 4.7 | 3.82 | 9.4 |
| II | 0.86 | 29.7 | 6.5 | 2.83 | 6.1 |
| III | 1.13 | 29.7 | 5.2 | 2.63 | 7.7 |
| IV | 1.39 | 29.7 | 4.5 | 2.06 | 9.0 |
| V | 0.81 | 29.7 | 3.8 | 1.44 | 10.7 |
| VI | 0.86 | 31.7 | 6.2 | 4.67 | 7.0 |
| VII | 1.13 | 31.7 | 4.2 | 3.49 | 10.6 |
| VII | 0.8 | 31.7 | 3.7 | 2.82 | 12.1 |

From the above Table, it is apparent that it is possible to attain permeate containing as little as 4.7 w % DMC when charging a solution containing 31.7 w % DMC—this being attained at a Flux of 3.82 kmh.

EXAMPLES IX-XVII

In this series of Examples, the procedure of Example I is followed except:

(i) In these Examples, the poly(4-vinyl pyridine) used was the Reilline 4200 brand, in concentration of 20 w % solids in methanol, which was diluted with methanol to yield a 10 w % stock solution;

(ii) the mole ratio MR in Examples IX, XII, and XV is 0.86; and in Examples XI, XIV, and XVII; it is 1.39;

(iii) the feed in Examples IX-XI contains 12.2 w % methanol, 67.9 w % $C_5$ hydrocarbons, and 19.8 w % methyl t-butyl ether (MTBE), in Examples XII-XIV, 8.2 w % methanol, 71.7 w % $C_5$ hydrocarbons, and 20.1 w % MTBE and in Examples XV-XVII, 8.0 w % methanol, 70.5 w % $C_5$ hydrocarbons, and 21.5 w % MTBE;

(iv) Separation Temperature is 35° C. in Examples IX-XIV and 45° C. in Examples XV-XVII.

TABLE

Support: Daicel DUY-L polyacrylonitrile
Reilline 4200 brand of polymer, ca 20%
poly(4-vinyl pyridine) PVP solids in MeOH
Coating: 3 mil
10 w % PVP in MeOH used as stock solution
Cure conditions: 125° C./2 min

| Example | MR | Feed W % | | | Permeate W % | | | Flux | Sep |
|---|---|---|---|---|---|---|---|---|---|
| | | MeOH | $C_5$ | MTBE | MeOH | $C_5$ | MTBE | | |
| IX | 0.86 | 12.2 | 67.9 | 19.8 | 76.4 | 18.4 | 5.2 | 1.58 | 23.3 |
| X | 1.13 | 12.2 | 67.9 | 19.8 | 98.4 | 1.4 | 0.3 | 2.06 | 442 |
| XI | 1.39 | 12.2 | 67.9 | 19.8 | 97.9 | 1.7 | 0.4 | 1.85 | 336 |
| XII | 0.86 | 8.2 | 71.7 | 20.1 | 63.6 | 28.2 | 8.3 | 0.65 | 19.6 |
| XIII | 1.13 | 8.2 | 71.7 | 20.1 | 97.9 | 1.8 | 0.3 | 1.47 | 552 |
| XIV | 1.39 | 8.2 | 71.7 | 20.1 | 93.3 | 5.1 | 1.6 | 1.10 | 156 |
| XV | 0.86 | 8.0 | 70.5 | 21.5 | 67.7 | 23.9 | 8.4 | 0.65 | 24.1 |
| XVI | 1.13 | 8.0 | 70.5 | 21.5 | 96.8 | 2.5 | 0.6 | 1.59 | 348 |
| XVII | 1.39 | 8.0 | 70.5 | 21.5 | 91.8 | 6.4 | 1.8 | 1.21 | 129 |

From the above Table, the following conclusions may be drawn:

(i) It is possible to treat a charge containing as much as 12.2 w % methanol and obtain a permeate containing as much as 98.4 w % methanol;

(ii) it is possible to treat a charge containing as much as 67.9 w % $C_5$ hydrocarbons and 19.8 w % MTBE and obtain a permeate containing as little as 1.4 w % $C_5$ hydrocarbons and 0.3 w % MTBE;

(iii) it is possible to obtain separation of this magnitude at a flux as high as 2.06 kmh.

Although this invention has been illustrated by reference to specific embodiments, it will be apparent to those skilled in the art that various charges and modifications may be made which clearly fall within the scope of the invention.

What is claimed is:

1. A method of concentrating a charge solution containing (i) an alcohol having less than three carbon atoms and (ii) an organic oxygenate selected from the group consisting of organic ethers, aldehydes, ketones, and esters which comprises maintaining a non-porous separating layer consisting essentially of a poly(vinyl pyridine) which has been cross-linked with an aliphatic polyhalide;

maintaining a pressure drop across said non-porous separating layer of poly(vinyl pyridine);

passing a charge solution containing (i) an alcohol having less than three carbon atoms and (ii) an organic oxygenate selected from the group consisting of organic ethers, aldehydes, ketones, and esters into contact with the high pressure side of said non-porous separating layer of poly(vinyl pyridine) whereby at least a portion of said alcohol in said charge solution and a lesser portion of organic oxygenate in said charge solution pass by pervaporation through said non-porous separating layer as a lean mixture containing more alcohol and less organic oxygenate than are present in said charge solution and said charge solution is converted to a rich liquid containing less alcohol and more organic oxygenate than are present in said charge solution;

recovering as permeate from the low pressure side of said non-porous separating layer, said lean mixture containing more alcohol and less organic oxygenate than are present in said charge solution, said lean mixture being recovered in vapor phase at a pressure below the vapor pressure thereof; and recovering as retentate from the high pressure side of said non-porous separating layer said rich liquid containing a lower alcohol content and a higher organic oxygenate content than are present in said charge solution.

2. The method claimed in claim 1 wherein said non-porous separating layer is a homopolymer of 4-vinyl pyridine which layer has been cross-linked with an aliphatic polyhalide.

3. The method claimed in claim 1 wherein said non-porous separating layer is a homopolymer of 4-vinyl of molecular weight $\overline{M}_v$ of 100,000-300,000 which layer has been cross-linked with an aliphatic polyhalide.

4. The method claimed in claim 1 wherein said non-porous separating layer is a copolymer of 4-vinyl pyridine and an ethylenically unsaturated monomer which layer has been cross-linked with an aliphatic polyhalide.

5. The method claimed in claim 1 wherein said non-porous separating layer consists essentially of a poly(vinyl pyridine) cross-linked with an aliphatic dihalide.

6. The method claimed in claim 1 wherein said non-porous separating layer is cross-linked with an aliphatic dihalide containing 2-10 carbon atoms.

7. A method claimed in claim 1 wherein said non-porous separating layer is cross-linked with a dibromobutane.

8. The method claimed in claim 1 wherein said organic oxygenate is an ether.

9. The method claimed in claim 1 wherein said ether is methyl t-butyl ether.

10. The method claimed in claim 1 wherein said organic oxygenate is an ester.

11. The method claimed in claim 1 wherein said ether is dimethyl carbonate.

12. The method claimed in claim 1 wherein said separating layer has a thickness of about 1–10 microns.

13. The method claimed in claim 1 wherein said poly(4-vinyl pyridine) which has been crosslinked is supported on a porous support layer.

14. The method in claim 13 wherein said porous support layer is a polyacrylonitrile polymer.

15. The method claimed in claim 14 wherein said porous support layer is a polyacrylonitrile polymer of molecular weight $\overline{M}_n$ of 5,000–100,000 and of molecular weight cut off of less than about 100,000.

16. A method of concentrating a charge solution containing (i) methanol and (ii) dimethyl carbonate or methyl t-buty ether as organic oxygenate which comprises maintaining a non-porous separating layer consisting essentially of cast poly(4-vinyl pyridine) which has been crosslinked with dibromobutane in the presence of sulfuric acid catalyst, said separating layer being supported on a porous support layer of polyacrylonitrile;

maintaining a pressure drop across said separating layer and said porous support layer;

passing charge solution into contact with the high pressure side of said non-porous separating layer whereby at least a portion of the methanol in said charge solution and a lesser portion of organic oxygenate in said charge solution passes by pervaporation through non-porous separating layer as a lean mixture containing more methanol and less organic oxygenate than are present in said charge solution and said charge solution is converted to a rich liquid containing less methanol and more organic oxygenate than are present in said charge solution;

recovering as permeate from the low pressure side of said non-porous separating layer said lean mixture containing more methanol and less organic oxygenate than are present in said charge solution, said lean mixture being recovered in vapor phase at a pressure below the vapor pressure thereof; and recovering as retentate from the high pressure side of said non-porous separating layer said rich liquid containing a lower methanol content and a higher organic oxygenate content than are present in said charge solution.

* * * * *